United States Patent

Jacksier et al.

[11] Patent Number: 6,153,167
[45] Date of Patent: Nov. 28, 2000

[54] GENERATION OF METAL-CARBONYL STANDARDS FOR THE CALIBRATION OF SPECTROSCOPIC SYSTEMS

[75] Inventors: Tracey Jacksier, Lisle; Reha Tepe, Willow Springs; David N. Vassallo, Glenview, all of Ill.

[73] Assignees: American Air Liquide, Walnut Creek, Calif.; L'Air Liquide, Societe Anonyme pour l'Etude et, l'Exploitation des Procedes Georges Claude, Paris, France

[21] Appl. No.: 09/264,309

[22] Filed: Mar. 8, 1999

Related U.S. Application Data

[60] Provisional application No. 60/085,268, May 12, 1998.

[51] Int. Cl.[7] .............................. C09K 3/00; C01G 1/04; B01J 31/00; C21B 15/04; B22F 1/00
[52] U.S. Cl. ........................... 423/417; 502/161; 75/413; 75/362; 252/372
[58] Field of Search ........................... 423/417; 502/161; 75/413, 362; 252/372

[56] References Cited

U.S. PATENT DOCUMENTS

| | | |
|---|---|---|
| 2,242,115 | 5/1941 | Danciger ........................... 23/203 |
| 2,378,053 | 6/1945 | Wallis et al. . |
| 2,395,999 | 3/1946 | Fill .................................. 23/203 |
| 3,839,077 | 10/1974 | Robinson ........................... 117/110 |
| 4,045,541 | 8/1977 | Mercer . |
| 5,093,101 | 3/1992 | Knott et al. ...................... 423/647 |
| 5,560,961 | 10/1996 | Adel et al. ....................... 427/304 |

FOREIGN PATENT DOCUMENTS

| | | |
|---|---|---|
| 861495 | 2/1961 | United Kingdom . |
| 897204 | 5/1962 | United Kingdom . |

OTHER PUBLICATIONS

Schaefer, "Determination of Traces of Tetracarbonylnickel and Pentacarbonyliron in Streams of Fluids Such as Synthesis Gas," Fresenius Z. Anal Chem, vol. 335, No. 7, pp. 785–790 (1989).

Communication from EPO dated Mar. 27, 2000—European Search Report.

*Primary Examiner*—Steven P. Griffin
*Assistant Examiner*—Jonas N. Strickland
*Attorney, Agent, or Firm*—Jeffrey L. Wendt

[57] ABSTRACT

Methods and apparatus for preparing gaseous compositions comprising a metal carbonyl, preferably at ppm concentration, are disclosed. The methods comprise placing metal, preferably in the form of filings, of the metal carbonyl to be produced into a first test vessel at a first temperature, and then pressurizing the first test vessel with a gas comprising carbon monoxide from a carbon monoxide source vessel. The contents of the first vessel are then heated to a second temperature and at a rate sufficient to initiate metal carbonyl formation, thereby forming a gas composition comprising a metal carbonyl. The reaction is then quenched by transferring some of the gas composition comprising a metal carbonyl from the first test vessel to a second test vessel which is at a third temperature, the third temperature being lower than the second temperature. Finally, the gas composition is diluted in the second test vessel with an inert gas (preferably argon) from an inert gas source container.

11 Claims, 6 Drawing Sheets

GENERATION OF METAL-CARBONYL STANDARDS FOR THE CALIBRATION OF SPECTROSCOPIC SYSTEMS

This application claims the benefit of U.S. Provisional Application No. 60/085,268, filed May. 12, 1998.

BACKGROUND OF THE INVENTION

1. Brief Description of the Invention

A method has been developed for the safe generation of metal carbonyl standards for the calibration of iron pentacarbonyl and nickel tetracarbonyl in CO by analylical methods such as FTIR, gas chromatography (GC), and mass spectroscopy (MS). Additionally these compounds can be used for the calibration of other direct introduction spectroscopic systems including but not limited to the sealed inductively coupled plasma (ICP), direct injection ICP-MS, and direct introduction ICP-AES.

2. Related Art

The literature describes two methods to produce pure carbonyls for commercial scale use.

A method for the production of iron carbonyl [$Fe(CO)_5$] was described by Walls et al. (U.S. Pat. No. 2,378,053). They described a procedure for the production by passing CO over the metal of the carbonyl desired. The exact conditions of temperature and pressure were found to depend of the particular metal. Walls et al. described that the production of Nickel carbonyl [$Ni(CO)_4$] proceeded easier than that for iron carbonyl. Reactions at atmospheric pressure and temperatures not to exceed 50° C. could be used although it was common to use higher temperatures and pressures. It was also recognized that the reaction of Ni+CO and Fe+CO to produce the respective carbonyls proceeded by different kinetic factors. Even in the presence of S or S containing compounds, which were observed to increase the rate of reaction, these processes were deemed impractical for industrial applications by the authors.

British Patent 897,204 describes the preparation of chrome carbonyl [$Cr(CO)_6$]. Previous to this patent chrome carbonyls had been formed by direct combination of CO with a salt of the metal in the presence of a strong reducing agent such as Li, Na or lithium aluminum hydroxide. The '204 patent describes preparing the carbonyl from a Cr/Fe alloy which contained less than 40% Cr by weight in the presence of an aromatic sulphonic acid and an alkali metal hydroxide at temperatures between 200–300° C. and pressures between 500–3000 atm. They noted that utilizing chrome alone (not in the presence of an alloy) did not give significant yields. The Cr/Fe alloy produced iron carbonyl and chrome carbonyl.

It has been observed by the present inventors that carbon monoxide (CO) filled in carbon steel vessels has the tendency to produce metal carbonyls, particularly iron carbonyl. There is a need in the semiconductor manufacturing art for determination of Fe and Ni as the carbonyl species in CO. Standards for calibrating laboratory equipment, such as FTIR, GC, ICP, ICP-MS, and ICP-AES, for the determination of metal carbonyl compounds, however are not commercially available. While it is possible to obtain pure iron pentacarbonyl, it is extremely toxic. Nickel tetracarbonyl, however is not stable and is not available as the pure source and is also extremely toxic. In order to prepare a ppm (v/v) standard of iron pentacarbonyl the liquid must be handled. It is not possible to prepare such a standard for nickel tetracarbonyl owing to the unavailability of the source starting material.

It would be a significant advance in the spectroscopic arts if a method were developed for the production of metal carbonyls, such as Fe and Ni carbonyls, at ppm levels which are stable for no less than 2 weeks.

SUMMARY OF THE INVENTION

In accordance with the present invention, methods of generating gaseous, compositions comprising ppm levels of metal carbonyls are presented which overcome problems in the prior art.

One aspect of the invention is a method of preparing gaseous compositions comprising a metal carbonyl, preferably at ppm concentration, the method comprising the steps of:

(a) placing metal, preferably in the form of filings, of the metal carbonyl to be produced into a first test vessel at a first temperature;

(b) pressurizing the first test vessel with a gas comprising carbon monoxide from a carbon monoxide source vessel;

(c) heating the contents of the first test vessel to a second temperature and at a rate sufficient to initiate metal carbonyl formation, thereby forming a gas composition comprising a metal carbonyl;

(d) quenching the reaction of the carbon monoxide with the metal by transferring some of the gas composition comprising a metal carbonyl from the first test vessel to a second test vessel which is at a third temperature, the third temperature being lower than the second temperature; and (e) diluting the gas composition comprising the metal carbonyl in the second test vessel with an inert gas (preferably argon, nitrogen, helium, or mixture thereof) from an inert gas source container.

It will be appreciated by those skilled in the art that more than one metal carbonyl can be produced simultaneously using the inventive method.

Preferred are methods in accordance with the invention wherein the first test vessel is a stainless steel test vessel, and the second test vessel is an aluminum test vessel.

Particularly preferred are methods in accordance with the invention wherein the metal is selected from the group consisting of Fe, Ni, Os, Ru, Ir, V, Mn, Cr, Co, Mo, and W, and wherein the metal carbonyl is selected from the group consisting of carbonyls of Fe, Ni, Os, Ru, Ir, V, Mn, Cr, Co, Mo, and W.

Preferably, the metal carbonyl is iron pentacarbonyl or nickel tetracarbonyl.

The physical form and amount of the metal influences the kinetics of the reaction of the metal with the carbon monoxide. Preferred methods of the invention are those wherein the metal used to produced the carbonyl is in the form of a powder, having a mesh size ranging from about 100 to about 300 mesh (about 170 to about 60 micrometers), more preferably ranging from about 150 to about 250 mesh (about 100 to about 70 micrometers). Lower mesh sizes (higher average diameters of particles) tend to lower the rate of reaction, all other parameters being held constant, while higher mesh sizes (lower average particle diameters) tend to increase the reaction rate, due to surface area. The amount of metal present in the first test vessel also influences the reaction rate, with a higher amount present generally leading to higher production rate for the particular carbonyl of interest, although this has been found to be surprisingly not a linear relationship, as illustrated in the examples herein.

The temperature of the first test vessel, after the gas comprising carbon monoxide is introduced therein, is raised to at least 150° C., more preferably at least 250° C. The higher the temperature, and the greater the rise in temperature, the more metal carbonyl will be generated by the methods of the invention. The rate of increase of temperature is preferably at least 1° C. per minute of heating, more preferably at least 10° C., per minute of heating. The rate of heating does not have to be, but preferably is constant, and is preferably monitored with temperature indicating devices well known in the art.

The heating of the contents of the first test vessel may be accomplished by any means sufficient to do the job. Preferred methods include attaching a common electrical heating tape to the outside of the first test vessel, but other methods, such as radiation heating, immersion in an oven, or immersion in a heat transfer fluid, might have advantages in certain applications. A combination of these methods could also be contemplated.

Preferably the advancement and quenching of the metal carbonyl formation reaction are monitored by FTIR or other analytical technique.

The pressure in the first test vessel, which is essentially the carbon monoxide partial pressure, depends on the temperature to which the first test vessel is raised, but typically and preferably is at least 500 psig (34 atmospheres), more preferably at least 1000 psig (68 atmospheres). The pressure in the second test vessel is generally initially less than the pressure of the first test vessel the pressure, and is then raised by the addition of the inert gas. The final pressure of the gas composition comprising the metal carbonyl and the inert gas is typically and preferably above 1000 psig (34 atmospheres), but below about 2500 psig (170 atmospheres. As the metal carbonyls in general tend to be less stable at lower pressures, higher pressures are preferred. Of course this generally dictates more expensive test chambers.

A second aspect of the invention is a method of simultaneous production of nickel tetracarbonyl and iron pentacarbonyl, the method comprising the steps of:

(a) introducing iron and nickel into a first test vessel, preferably in the form of stainless steel powder;

(b) pressurizing the first test vessel with a gas comprising carbon monoxide from a carbon monoxide source vessel;

(c) heating the contents of the first test vessel to a second temperature and at a rate sufficient to initiate simultaneous nickel tetracarbonyl formation and iron pentacarbonyl formation, thereby forming a gas composition comprising nickel tetracarbonyl and iron pentacarbonyl;

(d) quenching the reaction of the carbon monoxide with the iron and nickel by transferring some of the gas composition comprising nickel tetracarbonyl and iron pentacarbonyl from the first test vessel to a second test vessel which is at a third temperature, the third temperature being at a temperature sufficient to significantly retard decomposition of the nickel tetracarbonyl and iron pentacabonyl (the third temperature preferably lower (preferably at room temperature, or about 20° C.) than the second temperature); and (e) diluting the gas composition comprising the nickel tetracarbonyl and iron pentacarbonyl in the second test vessel with an inert gas (preferably argon) from an inert gas source container.

A third aspect of the present invention are the gas compositions comprising metal carbonyls produced by the methods of the invention.

Further advantages and aspects of the invention will become apparent by reviewing the following description and claims.

DESCRIPTION OF THE PREFERRED EMBODIMENTS

There is a need in the semiconductor manufacturing art and in various other arts, for example heat treating, for a determination of the metal carbonyl species in carbon monoxide and other gases. Standards for the determination of these compounds, however, are not commercially available.

The present invention provides methods and apparatus for producing ppm (v/v) concentrations of metal carbonyls in carbon monoxide. The concentration preferably ranges from about 1 ppm up to about 1000 ppm, more preferably from about 10 ppm to about 300 ppm.

As used herein, the following terms have the meanings defined below unless another meaning is obvious from the context.

"ICP" means inductively coupled plasma spectroscopy.

"ICP-MS" means inductively coupled plasma—mass spectroscopy.

"ICP-AES" means inductively coupled plasma—atomic emission spectroscopy.

"FTIR" means Fourier transform infrared spectroscopy.

"Inert gas" means a gaseous composition lacking any component reactive with metal carbonyls. Examples include, but are not limited to, argon, helium, nitrogen, neon, xenon, and any combination and mixtures thereof The methods of the invention are better explained with reference to specific examples which follow.

EXAMPLES

Figure 1:
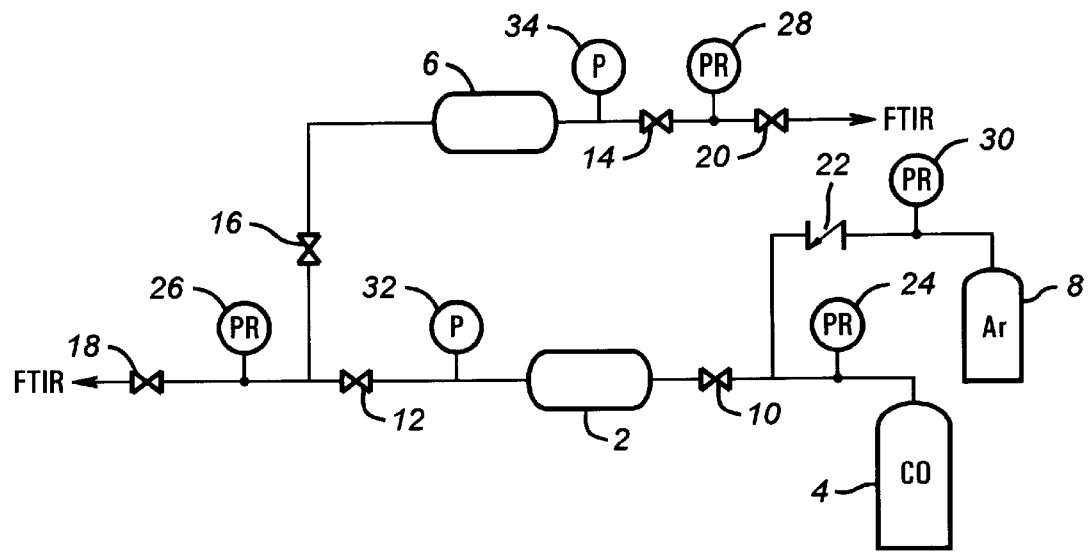
FIG. 1 illustrates a schematic of an apparatus used to practice the present invention.

The experimental setup is outlined in FIG. 1. Pure metal filings of the carbonyls to be prepared were placed into a stainless-steel test vessel 2 and the test vessel 2 subsequently filled with carbon monoxide from vessel 4. After some time the reaction was quenched by transferring some of the compound formed into a 500 mL aluminum test vessel 6 and diluted with argon supplied via argon vessel 8. The carbonyl formation is followed by FTIR analysis. Calculation of the carbonyl concentration is obtained through hydrolysis and FTIR (in the case of iron carbonyl) and by hydrolysis alone in the case of nickel carbonyl. Both the aluminum and stainless steel test vessels are preferably at least 500 ml volume and preferably resistant up to at least 3000 psi (200 atm). Needle valves, illustrated at 10, 12, 14, 16, 18, 20, and check valve 22, as well as pressure regulators 24, 26, 28, and 30, and pressure gauges 32 and 34, are preferably high temperature (greater than 250° C.) and high pressure (greater than 3000 psi, or 200 atm) resistant.

Example 1

Figure 2:
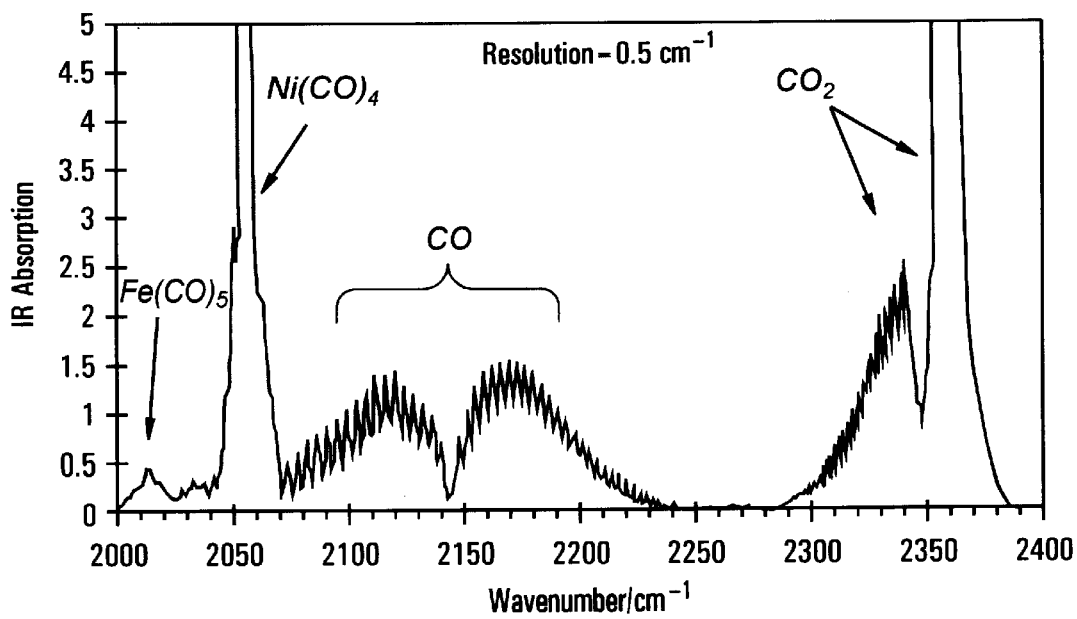
FIG. 2 illustrates the IR spectra of iron and nickel carbonyl produced using the method of the invention.
Figure 3:
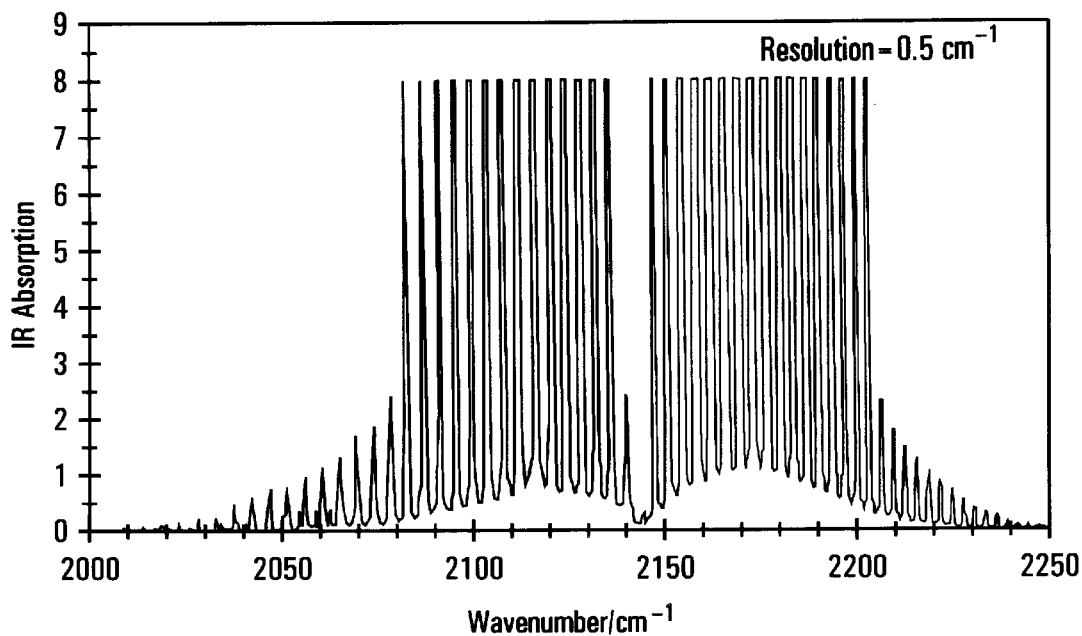
FIG. 3 illustrates the IR spectra of pure carbon monoxide.
Figure 4:
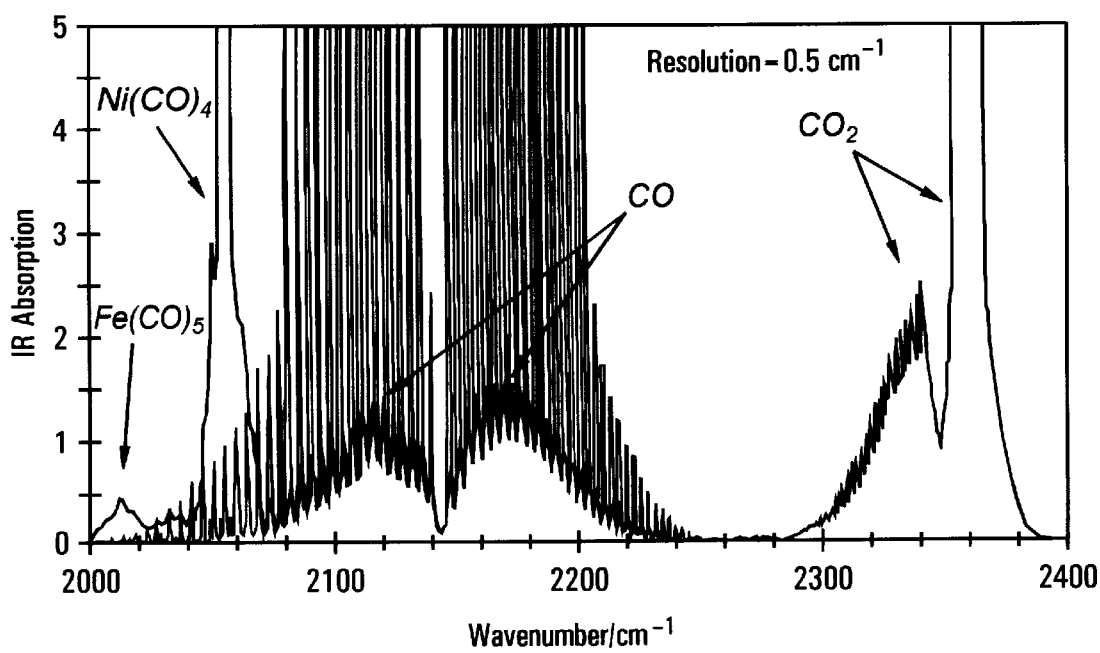
FIG. 4 illustrates the IR spectra of FIG. 3 superimposed on the IR spectra of FIG. 2.

A preliminary experiment to verify the potential of this technique was performed by placing 350 g of 316L stainless steel powder (200 mesh) [67.5% Fe, 13% Ni, 17% Cr, and 2.5% Mo] into a 500 mL stainless steel sample container 2 (FIG. 1) at 25° C. and pressurized with CO from vessel 4 up to P=1500 psi. The temperature was gradually increased at 20° C. per minute to 350° C. by placing heating tape around the sample vessel which increased the pressure to 3100 psi. The reaction was allowed to proceed for approximately 10 hours and the FTIR spectra observed. FIG. 2 clearly illustrates the formation of both iron and nickel carbonyls. Note that even though the concentration of nickel in the starting material was about 5 times lower than the iron concentration the production of nickel carbonyl was more significant. The IR absorption is illustrated for the 2000–2400 $cm^{-1}$ region. FIG. 3 illustrates the IR spectra of 2000–2250 $cm^{-1}$ of pure CO, illustrating the absence of iron or nickel carbonyl spectra features. FIG. 4 illustrates superimposed spectra of pure CO and CO containing both the nickel and iron carbonyls.

Example 2

Figure 5:
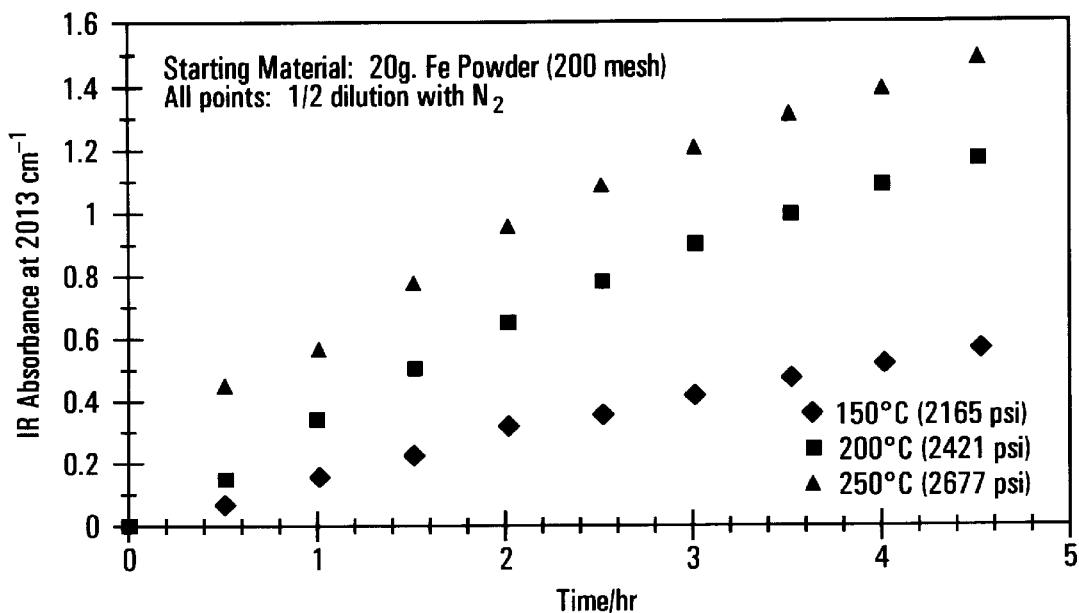
FIG. 5 illustrates the affect of temperature and pressure on the formation can iron pentacarbonyl.

Preparation of Iron Pentacarbonyl: Pure Iron fillings were added to test vessel 2 and pressurized under CO from vessel 4 in order to produce the iron pentacarbonyl. (The use of iron coupons was not sufficient to produce the compound). The effect of temperature and pressure was studied on 20 g of iron powder (200 mesh) for the production of iron pentacarbonyl. FIG. 5 illustrates the relationship of iron pentacarbonyl production as a function of temperature, pressure and time. Higher temperatures and pressures produced larger concentration of the carbonyl. It also appears as though at reaction times approaching 5 hours the reaction was beginning to reach a plateau.

Example 3

Figure 6:
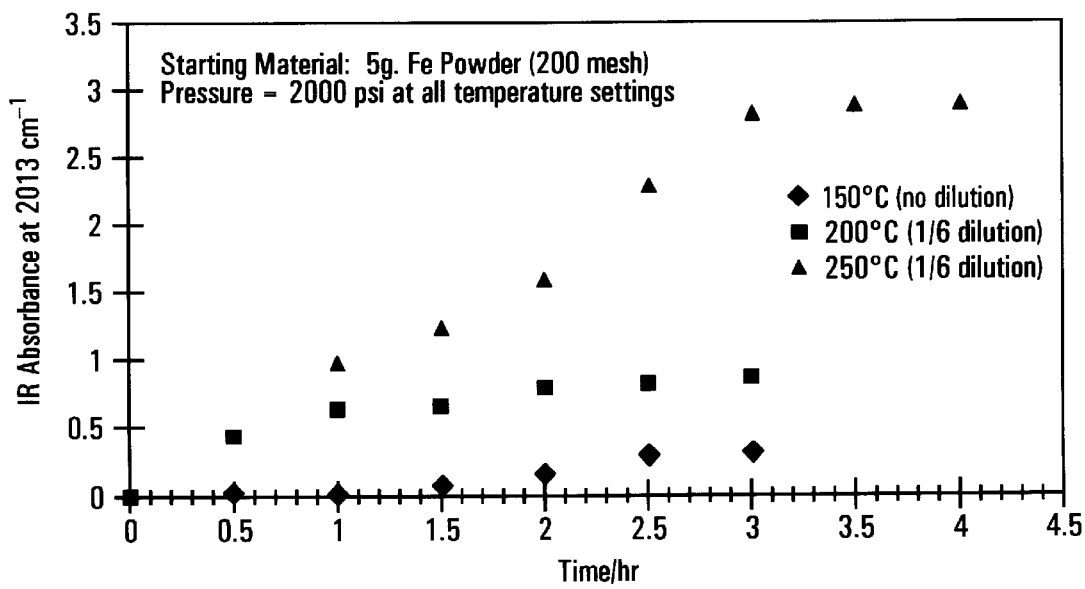
FIG. 6 illustrates the affect of temperature alone on the formation of iron pentacarbonyl.

The effect of temperature alone at pressures of 2000 psi is illustrated in FIG. 6 for 5 g of Fe powder. Surprisingly and quite unexpectedly, temperature alone appeared to have a more significant effect on the kinetics of the reaction than pressure.

Example 4

Figure 7:
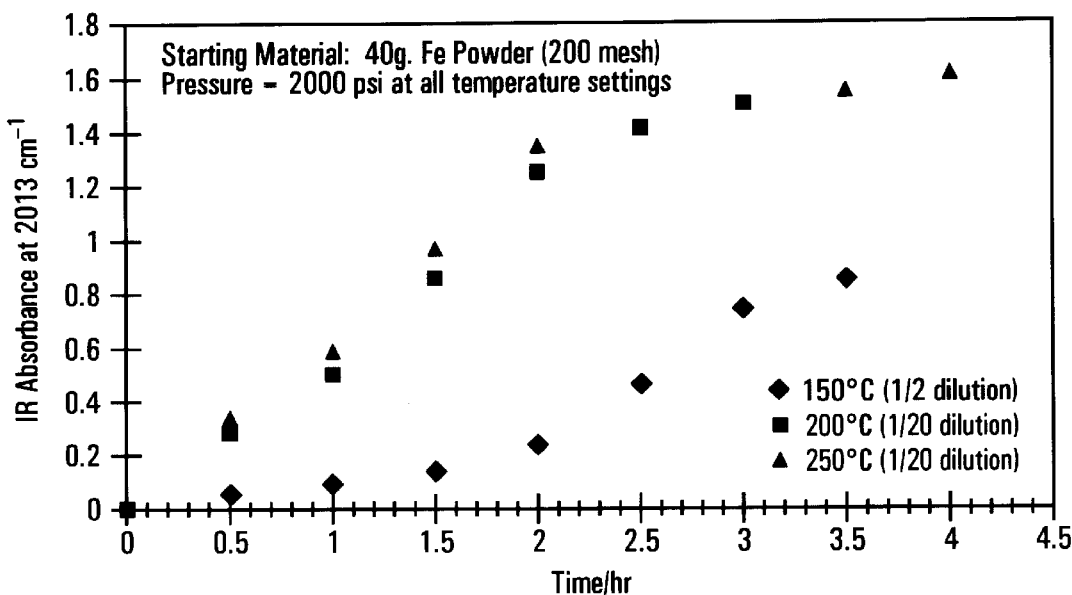
FIG. 7 illustrates the affect of weight of the starting material in the formation of iron pentacarbonyl in accordance with the practice of the invention.

The effect of weight of starting material on the production of iron pentacarbonyl can be seen by comparing FIGS. 6 and 7. Example 4 used the same methods and equipment as Example 3, but with 40 g Fe powder rather than 5 g. Note that the spectra in FIG. 6 are dilute by a factor of 6 and FIG. 7 are diluted by a factor of 20. Eight times the initial concentration of iron powder produced greater than a factor of 2 carbonyl at the same temperature and pressure. (After factoring in the 1/20 dilution factor (at 250° C.), the intensity reached with 40 g. iron powder as starting material is 1.6 (intensity)×20 (dilution factor)=32. Under the same conditions (i.e., temperature and pressure ) 5 g. iron powder resulted in an intensity value of 3 (intensity)×6 (dilution factor)=18. So, an eight time increase in starting material (40/5) resulted in approximately double the Fe(CO)5 concentration (32/18) after 4 hours.) Additionally the rate of carbonyl formation in 5 g sample appeared to level off at 200° C. and leveling off was absent in the 40 g sample.

Example 5

Figure 8:
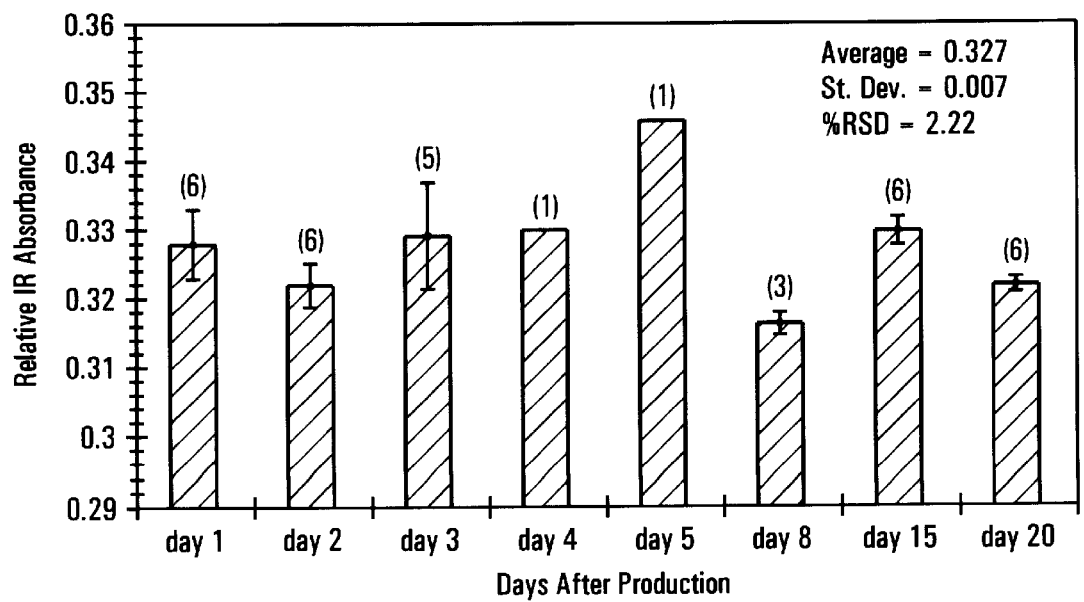
FIG. 8 illustrates the stability of iron pentacarbonyl produced in accordance with the present invention.

The stability of the iron pentacarbonyl produced by the methods of the invention was studied during 20 days. 20 g of iron powder (200 mesh) was placed in the stainless steel sample vessel 2 (FIG. 1). The vessel 2 was filled with 1120 psi of CO from vessel 4 and the temperature set at 250° C. by heating tape. The final pressure of the vessel after equilibrium with the temperature was measured to be 2000 psi (136 atm). After 2 hours in the reaction vessel, 700 psi of this sample was transferred to aluminum sample vessel 6 and the pressure of vessel 6 was increased to 2100 psi (143 atm) with argon from vessel 8. FIG. 8 illustrates excellent stability of the iron pentacarbonyl over 20 days. The concentration of iron pentacarbonyl produced was verified by FTIR and hydrolysis to be 80.7 ppm v/v $Fe(CO)_5$.

Example 6

Figure 9:
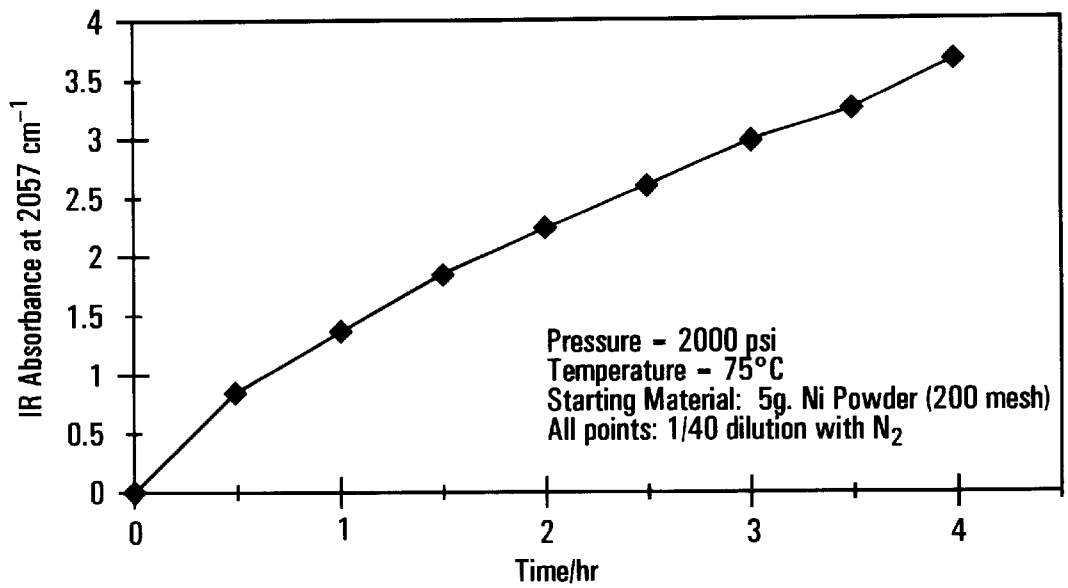
FIG. 9 illustrates a production curve of nickel tetracarbonyl produced in accordance with the present invention.
Figure 10:
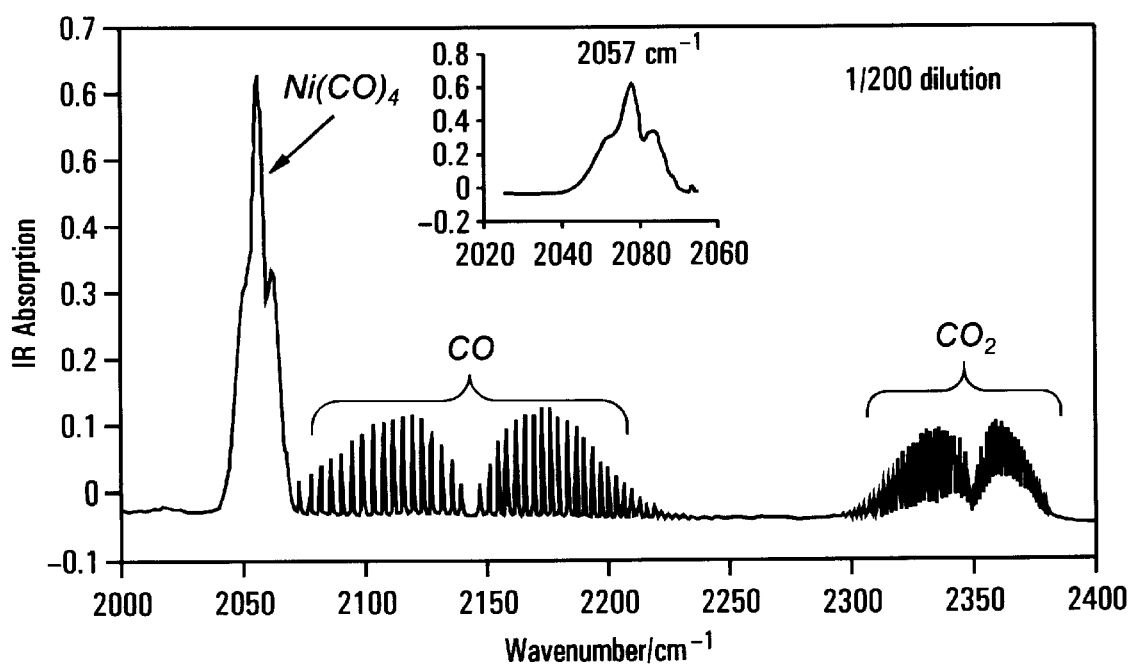
FIG. 10 illustrates the IR spectra of nickel tetracarbonyl in carbon monoxide, the nickel tetracarbonyl produced in accordance with the present invention.
Figure 11:
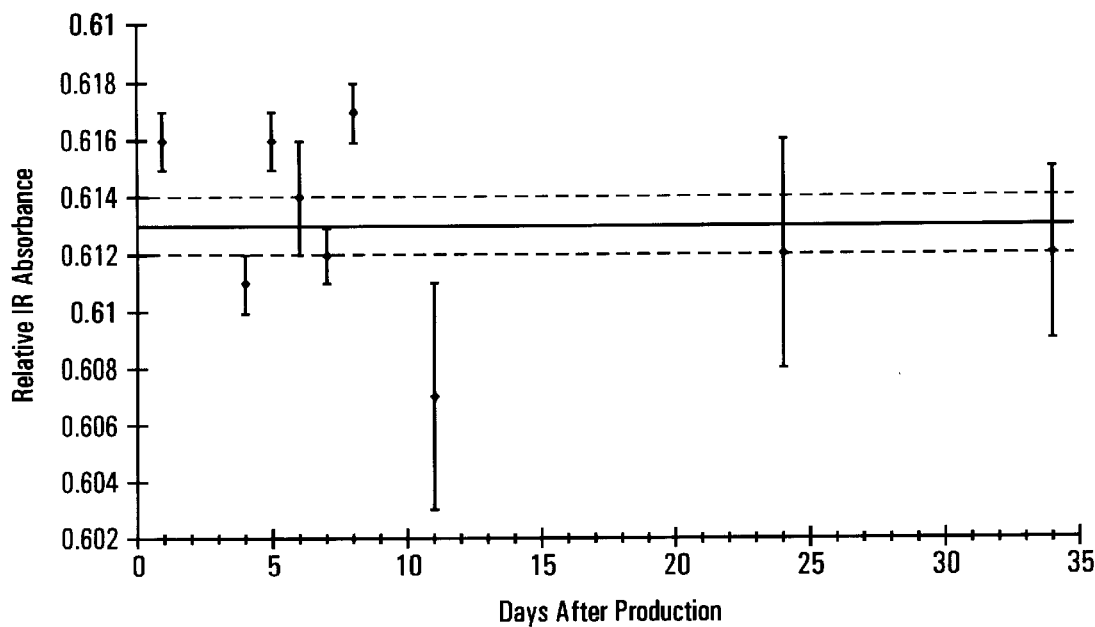
FIG. 11 illustrates the stability of nickel tetracarbonyl produced in accordance with the present invention.

Preparation of nickel tetracarbonyl: The experimental setup is illustrated in FIG. 1. Owing to the ease of formation of nickel tetracarbonyl in the initial experiment, FIG. 2, only 5 g of Ni powder (200 mesh) was placed into sample vessel 2 and pressurized with CO to 2000 psi (136 atm) at 75° C. The production curve is illustrated in FIG. 9 for 4 hours. The IR spectrum of the nickel tetracarbonyl produced is illustrated in FIG. 10. After production, 400 psi (27 atm) of $Ni(CO)_4$ was transferred to the aluminum sample vessel 6 and diluted by increasing the pressure to 2000 psi (136 atm) with argon from vessel 8. The stability was monitored during 35 days (FIG. 11). The relative standard deviation (RSD) was (0.59% after 35 days indicating excellent stability.

It is expected that the methods of the invention can be extended to formation of other metal carbonyl compounds, such as carbonyls of Os, Ru, Ir, V, Mn, Cr, Co, Mo, and W, however the present invention is particularly useful to generate metal carbonyls of iron and nickel as those carbonyls are volatile at room temperature.

Figure 12:
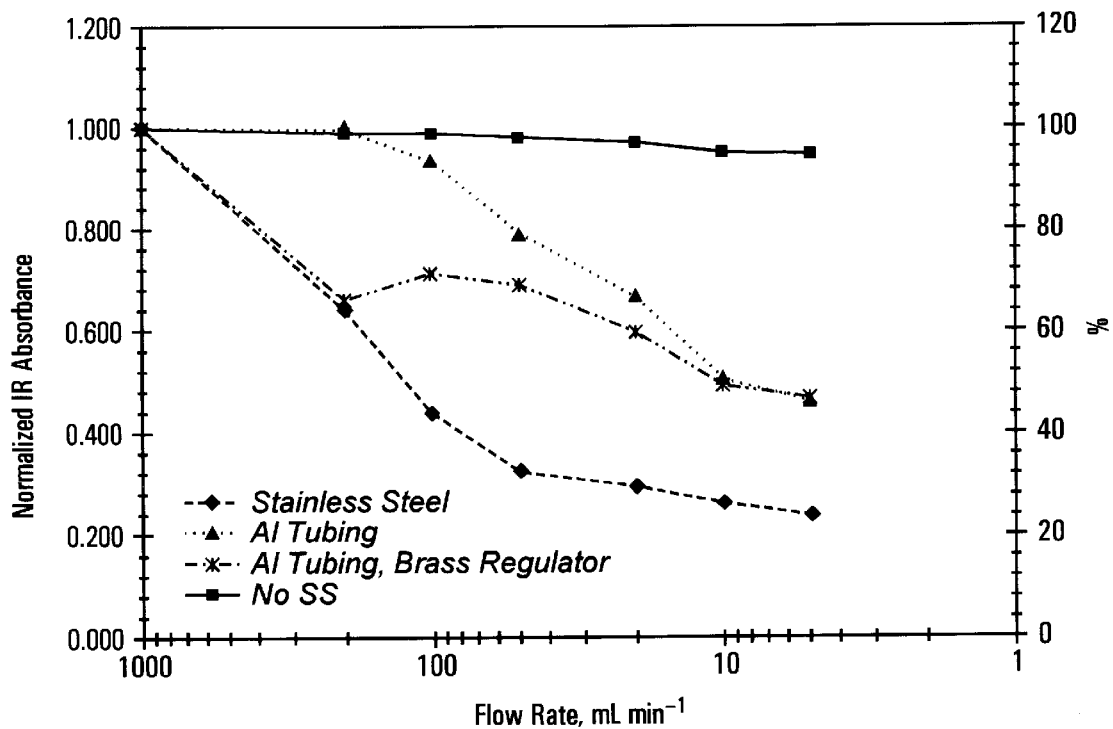
FIG. 12 illustrates that when stainless steel components are removed from the apparatus of the invention from the aluminum sample chamber to the analyzer, decomposition of the formed metal carbonyl decreases.

As regards the formation of nickel tetracarbonyl, further observations showed that after nickel tetracarbonyl was generated using the methods and apparatus of the invention, one embodiment being illustrated in FIG. 1, some of it was transferred to the aluminum sample cylinder (vessel 6) as explained in the invention disclosure. The original setup consisted of parts (e.g. regulator, tube, connectors, valves and mass flow controller) that were made of stainless steel (SS) between the aluminum vessel and the FTIR cell. The length of tubing was approximately 1.5–2 meters. It was observed that the IR signal substantially changed at different flowrates of the carbonyl through the tubing. The IR signal dropped drastically when the flow rate was decreased (see FIG. 12). At 5 mL/min, almost 80% of the compound was decomposed. This can be possibly attributed to the surface reaction between Ni(CO)4 and the stainless steel surfaces.

After this observation was made, the stainless steel parts have been replaced by either brass or aluminum counterparts. The attached figure shows that as the Stainless steel parts were removed from the system after the aluminum vessel the effect of signal drop with decreasing flow rate diminishes. When the last stainless steel part, in other words, the regulator, was replaced with a calibrated needle valve the signal did not decrease more than 4% between 1000 and 5 mL/min. This evidence suggested that the best mode of the method and apparatus of the invention would be removal of all stainless steel components between the aluminum sample chamber and the analyzer.

The invention has been described with reference to the examples and preferred embodiments, but the invention is not limited to those specifics, and should not be read to unduly limit the scope of the claims.

What is claimed is:

1. A method of preparing gaseous compositions comprising a metal carbonyl, at ppm concentration, the method comprising the steps of:
   (a) placing metal of the metal carbonyl to be produced into a first test vessel at a first temperature, the metal being of a form selected from the group consisting of powders and filings;
   (b) pressurizing the first test vessel with a gas comprising carbon monoxide from a carbon monoxide source vessel;
   (c) heating the first test vessel to a second temperature and at a rate sufficient to initiate reaction of carbon monoxide with the metal to promote metal carbonyl formation, thereby forming a gas composition comprising a metal carbonyl;
   (d) quenching the reaction of the carbon monoxide with the metal by transferring some of the gas composition comprising a metal carbonyl from the first test vessel to a second test vessel which is at a third temperature, the third temperature being lower than the second temperature; and
   (e) diluting the gas composition comprising the metal carbonyl in the second test vessel with an inert gas from an inert gas source container.

2. Method in accordance with claim 1, wherein the first test vessel is a stainless steel test vessel.

3. Method in accordance with claim 1, wherein the second test vessel is an aluminum test vessel.

4. Method in accordance with claim 1, wherein the metal is selected from the group consisting of Fe, Ni, Os, Ru, Ir, V, Mn, Cr, Co, Mo, and W and the metal carbonyl is selected from the group consisting of carbonyls of Fe, Ni, Os, Ru, Ir, V, Mn, Cr, Co, Mo, an W.

5. Method in accordance with claim 4, wherein the metal carbonyl is iron pentacarbonyl.

6. Method in accordance with claim 5, wherein the iron metal used to produced the iron pentacarbonyl is in the form of a powder.

7. Method in accordance with claim 5, wherein the second temperature is at least 150° C.

8. Method in accordance with claim 7, wherein the second temperature is at least 250° C.

9. Method in accordance with claim 4, wherein the metal carbonyl is nickel tetracarbonyl.

10. Method in accordance with claim 1, wherein the heating of the first test vessel is by an electrical heating tape device.

11. A method of simultaneous production of nickel tetracarbonyl and iron pentacarbonyl, the method comprising the steps of:
    (a) introducing stainless steel powder comprising iron and nickel into a first test vessel;
    (b) pressurizing the first test vessel with a gas comprising carbon monoxide from a carbon monoxide source vessel;
    (c) heating the first test vessel to a second temperature and at a rate sufficient to initiate simultaneous nickel tetracarbonyl formation and iron pentacarbonyl formation, thereby forming a gas composition comprising nickel tetracarbonyl and iron pentacarbonyl;
    (d) quenching the reaction of the carbon monoxide with the iron and nickel by transferring some of the gas composition comprising nickel tetracarbonyl and iron pentacarbonyl from the first test vessel to a second test vessel which is at a third temperature, the third temperature being at a temperature sufficient to significantly retard decomposition of the nickel tetracarbonyl and iron pentacarbonyl; and
    (e) diluting the gas composition comprising the nickel tetracarbonyl and iron pentacarbonyl in the second test vessel with an inert gas from an inert gas source container.

* * * * *